United States Patent [19]

Haskell et al.

[11] 4,301,315

[45] Nov. 17, 1981

[54] METHOD OF PRODUCING HIGH OCTANE ALKYLATE GASOLINE

[75] Inventors: Donald M. Haskell; Floyd Farha, Jr., both of Bartlesville, Okla.

[73] Assignee: Phillips Petroleum Company, Bartlesville, Okla.

[21] Appl. No.: 835,940

[22] Filed: Sep. 22, 1977

[51] Int. Cl.³ .......................... C07C 2/06; C07C 2/56
[52] U.S. Cl. .................................. 585/304; 585/324; 585/326; 585/332; 585/510; 585/617; 585/709
[58] Field of Search .................... 260/683.4 R, 683.43, 260/680 R, 677 R, 683.48, 683.61, 683.49, 683.1, 683.15 D; 585/304, 324, 326, 332, 510, 617, 709

[56] References Cited

U.S. PATENT DOCUMENTS

| | | | |
|---|---|---|---|
| 2,356,374 | 8/1944 | Blount | 260/683.43 |
| 2,363,300 | 11/1944 | Dunstan et al. | 260/683.1 |
| 2,382,899 | 8/1945 | Newman | 260/683.4 |
| 2,389,984 | 11/1945 | Jones | 260/683.4 |
| 2,403,501 | 7/1946 | Clarke | 260/683.4 |
| 3,452,113 | 6/1969 | Godin | 260/677 R |
| 3,488,403 | 1/1970 | Franz et al. | 260/683.1 |
| 3,660,520 | 5/1972 | Hemminger | 260/683.43 |
| 3,709,952 | 1/1973 | Desgrandchamp et al. | 260/683.15 D |
| 4,054,613 | 10/1977 | Haskell et al. | 260/680 R |

*Primary Examiner*—Curtis R. Davis

[57] ABSTRACT

A stream comprising isobutylene and n-butenes is processed to effect dimerization of the isobutylene, and the resulting isobutylene dimer is fed to an alkylation step.

5 Claims, 1 Drawing Figure

METHOD OF PRODUCING HIGH OCTANE ALKYLATE GASOLINE

FIELD OF THE INVENTION

This invention relates to a method of producing a high octane gasoline mixture, utilizing an initial feed stream comprising isobutylene and normal butenes.

In one aspect, the invention relates to a method of producing the combination of a high octane gasoline mixture and 1,3-butadiene from an initial feed stream comprising isobutylene and normal butenes. In another aspect it relates to producing the combination of a high octane gasoline mixture and high purity butene-1 from such an initial feed stream which also contains butene-1.

In another aspect, it relates to producing the combination of 1,3-butadiene, a high octane gasoline, and high purity butene-1 from an initial feed stream comprising isobutylene, butene-1, and butenes-2.

BACKGROUND OF THE INVENTION

Olefin-containing streams from refineries often contain butenes-2 and isobutylene in the presence of other four carbon compounds such as butene-1 and n-butane. It is desirable to use parts of such a stream to produce a high octane alkylate gasoline. It is also desirable to separate isobutylene from this mixture, so that the n-butenes can be used to produce valuable 1,3-butadiene. Alternatively, it may be desirable to use a portion of the n-butenes to produce some valuable high purity butene-1.

The presence of isobutylene in a stream to be sent to a butadiene manufacturing process is undesirable since the isobutylene is not useful in the formation of butadiene. Also, to obtain high purity butene-1, the isobutylene must be separated. Isobutylene and butene-1 have very close boiling points, however; and their separation by fractional distillation is very difficult.

The present invention addresses all of these needs and problems and provides a good solution.

It is an object of the present invention to provide a method for producing 1,3-butadiene and a high octane alkylate gasoline from a four carbon olefin-containing stream from refineries. It is also an object to produce high purity butene-1 from such a stream.

STATEMENT OF THE INVENTION

According to the invention, an initial feed stream comprising isobutylene and certain n-butenes is subjected to a dimerization process, and the resulting dimers of isobutylene are separated from the 4-carbon hydrocarbons and used in an alkylation process to produce a high octane gasoline. At least a portion of the mixture remaining after removal of the dimers is used for production of butadiene and/or high purity butene-1.

PREFERRED EMBODIMENTS OF THE INVENTION

Figure 1:
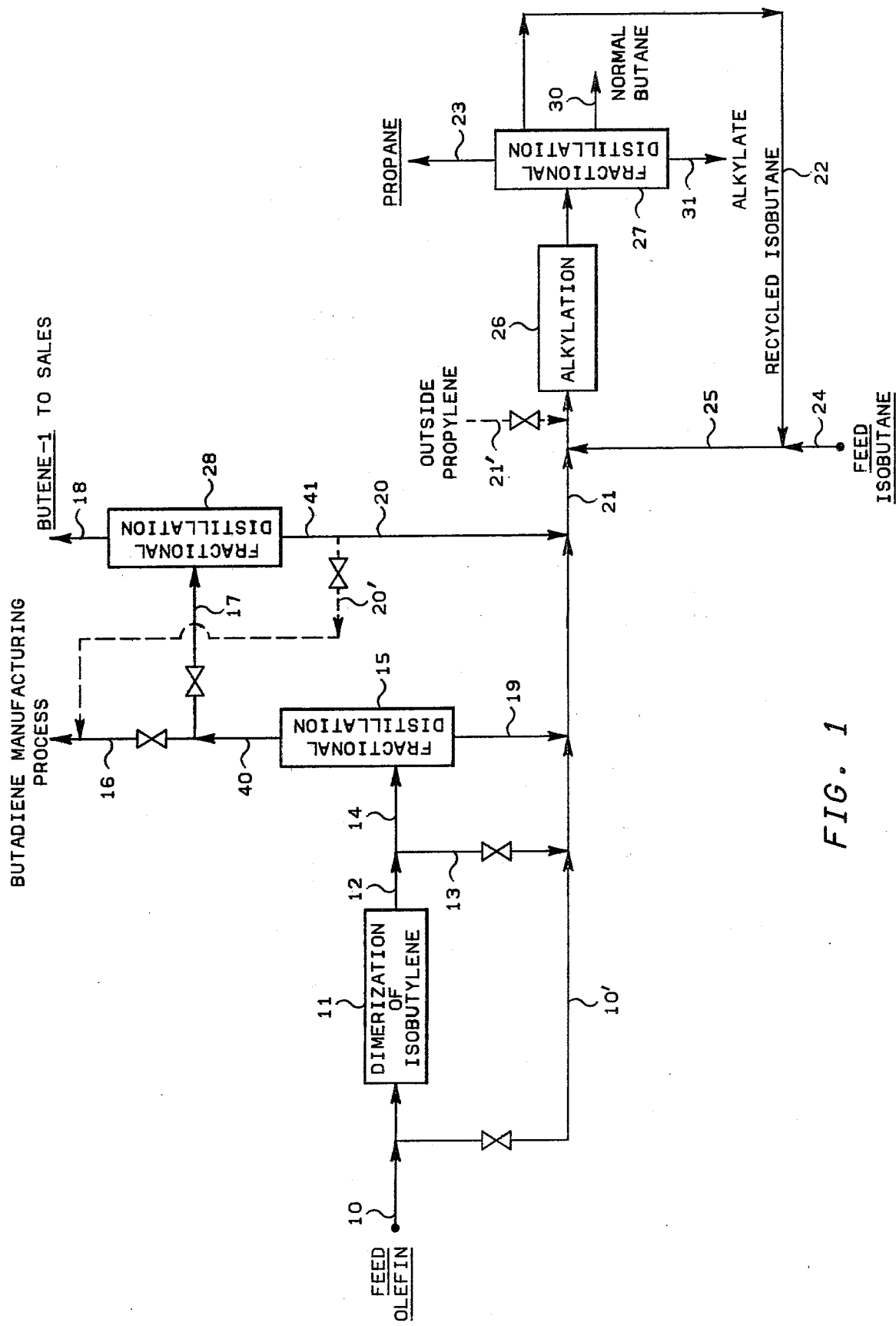
FIG. 1 is a diagrammatical illustration of the steps in the inventive process.

Referring to the drawing, a four carbon olefin-containing stream 10 from a refinery often comprises isobutylene, 1-butene, trans-2-butene, cis-2-butene, and normal butane. This stream is fed into a dimerization operation 11 which converts the isobutylene to two dimers, whereas the butene-1, butenes-2, and the normal butane do not substantially enter into the dimerization reaction. The resulting mixture after dimerization is labeled 12 in FIG. 1. Fractional distillation of that mixture is labeled 15. The butenes and normal butane distill overhead in a "second stream" 40, leaving behind the dimers, which are all charged to alkylation via 19. The "second stream" 40 can be charged to a butadiene manufacturing process via 16 to produce 1,3-butadiene, or (optionally) a part of that stream 17 can be further fractionally distilled 28 to separate high purity butene-1 18 for sale. The higher boiling portion of the fractionation mixture in 28 can all be sent to alkylation via 20, or alternately, a protion thereof can be sent to a butadiene manufacturing process via 20' to produce 1,3-butadiene.

The alkylation feed stream 21 can be fed by a number of streams: optional stream 10' (which contains a portion of the original feed olefin stream), optional stream 13 which contains a portion of the mixture after dimerization, stream 19 containing the distilled dimers, and stream 20 containing at least a portion of the butenes-2 and normal butane. Also, stream 21 can be optionally fed by outside propylene 21'. The alkylation stream is subjected to alkylation shown at 26 and is then fractionally distilled in 27 to remove overhead propane 23, an upper side stream of isobutane 22, alower side stream of normal butane vapor 30, and alkylate via 31. Recycled isobutane 22 can be fed (together with a feed isobutane and/or isopentane 24) back into the stream 21, via 25, to be alkylated.

The dimerization operation 11 serves three functions in converting isobutylene to dimers. One function is to permit the separation of the isobutylene from the close boiling butene-1. The dimerization reaction (as specified herein) quickly converts essentially all of the isobutylene to the dimers, wheras the 4-carbon normal olefins and normal butane do not appreciably enter into the reaction. And the produced dimers have a much higher boiling point than the remaining, unreacted 4-carbon hydrocarbons. Therefore, fractional distillation after dimerization permits an excellent separation of isobutylene, as the dimer, from the remainder of the 4-carbon hydrocarbons.

The second function of dimerization also involves the separation which is possible after the dimerization operation. Normal butenes to be used in the production of 1.3-butadiene should not contain isobutylene since it is not useful in the formation of butadiene. The third function of the dimerization reaction is in providing the dimers to be used in the alkylation step. It is known in the art that by adding isobutylene dimers to a given ratio of isoparaffin/olefin one can raise the octane number of the mixture. Alternatively, by adding isobutylene dimers, one can produce a given octane number with a lower ratio of isoparaffin/olefin than one could produce without the addition of the dimers.

The amounts that are charged to various steps in the operation depend upon what types of products are required and upon what amounts of reactants are available in the inital feed stream. For example, if more dimer is required in the alkylation process, more of stream 10 will be charged to dimerization and less (or none) of stream 10 will be sent directly into the alkylation stream 21 by way of 10'. Also, for example, "second stream" 40 will be split, depending on the requirements for 1,3-butadiene and/or high purity butene-1.

Therefore, streams 10', 13, and 20' represent optional steps in FIG. 1.

In the practice of the invention, the isobutylene dimerization can be any isobutylene dimerization known in the art which dimerizes isobutylene but which does not significantly affect the butenes that are present.

The isobutylene dimerization step can employ any suitable catalyst which is capable of dimerizing isobutylene. The preferred dimerization catalyst is one which will produce relatively high quantities of diisobutylene (2,4,4-trimethylpentene-1 and 2,4,4-trimethylpentene-2) with relatively small amounts of other $C_8$ isomers or higher isobutylene oligomers. Some examples of suitable dimerization catalysts are cold sulfuric acid; nickel-containing and rhodium-containing compounds activated with an aluminum alkyl; phosphoric acid on Kieselguhr; silica/alumina sometimes promoted with Ni, Co, Fe, Pt or Pd; activated natural clays plus activating substances such as ZnO; metallic phosphates such as those of iron (III) and cerium optionally supported on carriers such as activated carbon; bauxite; activated carbon alone and with metal halides such as $TiCl_3$; heteropolyacids such as silicotungstic acid on silica gel and phosphomolybdic acid; $BF_3.H_3PO_4$ and $BF_3.HPO_3$; dihydroxyfluoboric acid; HF and fluorides or oxyfluorides of S, Se, N, P, Mo, Te, W, V and Si boiling below 300° C.; $BF_3$-diethyl ether complexes; $BF_3$-hydrocarbon complexes; $BF_3$—$SO_2$; and $AlCl_3$ with cocatalysts such as diethyl ether, HCl and nitromethane. These catalysts and dimerization processes, including operaton conditions, are known in the art. The presently preferred catalyst is cold sulfuric acid or a soluble nickel compound activated with an aluminum alkyl, such as for example bis(tri-n-butylphosphine) nickel dichloride-ethylaluminum dichloride.

Depending upon the specific catalyst used, the dimerization is generally carried out at a temperature of 0°–230° F., at a pressure of 25–75 psig and with a contact time of 0.1 minute to 1 hour. Because isobutylene dimerizes much more readily than the normal butenes, the least severe conditions which will substantially completely convert the isobutylenes are preferred.

The alkylation step can be any suitable alkylation process, such as HF alkylation or $H_2SO_4$ alkylation. The preferred method is the conventional HF catalytic alkylation of isobutane with olefins (usually $C_3$ and $C_4$ olefins) and the isobutylene dimers. This method is preferred because with HF alkylation cooling water temperatures can be used and refrigeration, as needed in $H_2SO_4$ alkylation, is not required.

The HF alkylation should be carried out at a pressure sufficient to mainta in the liquid phase. A pressure within the range of above about 135 psig is preferred for this reason. A pressure of about 150 psig is more preferably used. There is no advantage to exceed to a great amount that pressure needed to maintain liquid phases at the alkylation temperature selected.

The temerature used in the alkylation step can be within the range of about −10 to about 150° F. because lower temperatures allow production of higher octane alkylate using the same isobutane/olefin ratio used at higher temperatures, or allow producction of the same octane alkylate at a lower isobutane/olefin mol ratio, as is known in the art of alkylation. For butylenes alkylate, each 10° F. rise in temperature decreases octane by about 0.5 numbers. A temperature of 150° F. can be used, but higher pressure is needed to maintain liquid phases; and octane value can fall off if the isobutane/olefin ratio is not increased. The excess isobutane which does not react with olefins to produce alkylate is fractionated from the alkylate and recycled. This fractionation is also very expensive. Plant economics will dictate the temperature and isobutane/olefin mol ratio used to produce the desired octane akylate. A temperature of about 85° F. is most preferred, because plant cooling water can be economically used to maintain 85° F. reaction temperature.

The contact time in the HF alkylation should preferably be from about 10 to 200 seconds, depending upon the type of conventional alkylation reactor used; and about 20 seconds is most preferred when using a riser-type reactor as described in U.S. Pat. No. 3,213,157, issued Oct. 19, 1965, to Phillips Petroleum Company.

In the HF alkylation, the isobutane/olefin mole ratio (including the isobutylene dimers) should preferably be within the range of about 4:1 to about 25:1 and more preferably about 10:1 because high isobutane/olefin ratios prevent olefin polymerization and allow production of high octane alkylate.

The ratio of HF to total hydrocarbon volume should be within the range of about 0.25:1 to about 8:1 and preferably about 4:1 because within these ratios the highest octane alkylate is produced.

The butadiene manufacturing process can be any butadiene manufacturing process.

The fractional distillations can be carried out by any method known in the art. The fractional distillation to separate the dimers in 15 will, for example, be carried out at a pressure of about 70 psig with a top temperature of about 120° F. and a bottom temperature of about 340° F. Likewise, the fractional distillation for separating high purity butene-1 in 28 can, for example, be at about 80 psig with a top temperature of about 120° F. and a bottom temperature of about 140° F. Further, the fractional distillation 27 to separate the alkylate gasoline can for example be at about 275 psig with a top temperature of about 125° F. and a bottom temperature of about 430° F.

CALCULATED EMBODIMENT

An illustrative calculated embodiment is given in Table I, showing possible uses of parts of a typical initial feed stream from a refinery. The numbers identifying the streams correspond to the numbers in FIG. 1.

The flow scheme and material balance are provided to illustrate the invention. The operation was "idealized" to simplify the "calculated" material balance. The material balance is based on operating dimerization unit 11 utilizing sulfuric acid and operating the unit at 500 psig and with a residence time within the reactor of about one minute and operating the HF alkylation unit 27 at a pressure of 150 psig; at a temperature of 90° F.; at a contact time of 40 seconds; at an isobutane to total olefin (including the isobutylene dimer) mol ratio of about 10:1, and an HF catalyst to total hydrocarbon volume ratio of about 4:1.

TABLE I

| Stream | \(Calculated Embodiment (Pounds Per Hour)\) | | | | | | | | | | | | | | | |
|---|---|---|---|---|---|---|---|---|---|---|---|---|---|---|---|
| | (10) | (12) | (13) | (14) | (16) | (17) | (18) | (19) | (20) | (21) | (22) | (24) | (25) | (23) | (30) | (31) |
| Component | | | | | | | | | | | | | | | | |
| Propane | 0 | 0 | 0 | 0 | 0 | 0 | 0 | 0 | 0 | 0 | 0 | 0 | 0 | 200 | 0 | 0 |
| Isobutene | 600 | 0 | 0 | 0 | 0 | 0 | 0 | 0 | 0 | 0 | 0 | 0 | 0 | 0 | 0 | 0 |
| n-Butane | 600 | 600 | 200 | 400 | 300 | 100 | 0 | 0 | 100 | 300 | 0 | 0 | 0 | 0 | 300 | 0 |
| Butene-1 | 6000 | 6000 | 2000 | 4000 | 3000 | 1000 | 1000 | 0 | 0 | 2000 | 0 | 0 | 0 | 0 | 0 | 0 |
| Butenes-2 | 7800 | 7800 | 2600 | 5200 | 3900 | 1300 | 0 | 0 | 1300 | 3900 | 0 | 0 | 0 | 0 | 0 | 0 |
| Isobutane | 0 | 0 | 0 | 0 | 0 | 0 | 0 | 0 | 0 | 0 | 59,000 | 5900 | 64,900 | 0 | 0 | 0 |
| Diisobutylene | 0 | 600 | 200 | 400 | 0 | 0 | 0 | 400 | 0 | 600 | 0 | 0 | 0 | 0 | 0 | 0 |
| Akylate | 0 | 0 | 0 | 0 | 0 | 0 | 0 | 0 | 0 | 0 | 0 | 0 | 0 | 0 | 0 | 12,200 |
| TOTAL | 15,000 | 15,000 | 5,000 | 10,000 | 7,200 | 2,400 | 1,000 | 400 | 1,400 | 6,800 | 59,000 | 5,900 | 64,900 | 200 | 300 | 12,200 |

This invention has been described in detail for purposes of illustration, but it is not to be construed as limited thereby. Rather, it is intended to cover reasonable changes and modifications which will be apparent to one skilled in the art.

One such modification is to combine the processes of the production of high octane alkylate gasoline plus the production of butadiene, and this is accomplished by closing the valve in path 17 and leaving the valve in path 16 open. Another modification is to combine the processes of the production of high octane gasoline plus the production of high purity butene-1, and this is accomplished by closing the valve in path 16 and leaving the valve in path 17 open. A third possibility is to leave the valves in both paths 16 and 17 open, thereby accomplishing the production of all three products. Further, when outside propylene is used, the valve in path 21' is open; otherwise, it is closed. When a portion of the original feed olefin stream is fed to the alkylation feed stream 21, the valve in path 10' is open; and otherwise, it is closed. Also, when a portion of the mixture after dimerization 12 is fed to the alkylation stream 21, the valve in path 13 is open; and otherwise, it is closed. And when a portion of the higher boiling portion of the fractionation mixture in 28 is fed to the butadiene manufacturing process, the valve in path 20' is open; and, otherwise, it is closed.

We claim:

1. A process for producing a high octane alkylate gasoline, 1,3-butadiene, and high purity butene-1 from a 4-carbon olefin-containing feed stream comprising isobutylene, butenes-2, and butene-1, said process comprising:
   (a) charging a first portion of said 4-carbon olefin-containing feed stream to an isobutylene dimerization reaction so as to form a first reaction mixture containing dimers;
   (b) fractionally distilling is a first fractional distillation zone at least a portion of said first reaction mixture so as to recover said dimers and to produce a second stream comprising said butenes-2 and said butene-2;
   (c) charging said dimers to an alkylation feed stream;
   (d) charging a first portion of said second stream to a butadiene reaction so as to form 1,3-butadiene as a product of said process;
   (e) charging a second portion of said 4-carbon olefin-containing feed stream to said alkylation feed stream;
   (f) charging said alkylation feed stream to an alkylation process so as to form a high octane alkylate gasoline; and
   (g) charging a second portion of said second stream to a second fractional distillation zone to produce a high purity butene-1 stream and to produce a third stream comprising butenes-2.

2. A process according to claim 1, wherein a first portion of said third stream is charged to said alkylation feed stream.

3. A process according to claim 2, wherein a second portion of said third stream is charged to said butadiene reaction.

4. A process according to claim 3 and including also the additional steps of recovering said high octane alkylate and of recovering said 1,3-butadiene.

5. A process according to claim 3 and including also the additional step of recovering said high octane alkylate gasoline.

* * * * *